(12) United States Patent
Su

(10) Patent No.: US 7,913,539 B2
(45) Date of Patent: Mar. 29, 2011

(54) APPARATUS FOR DROP TESTING AND METHOD UTILIZING THE SAME

(75) Inventor: Ting-Feng Su, Hsinchu (TW)

(73) Assignee: Powertech Technology Inc., Hsinchu Industrial Park, Hukou Shiang (TW)

( * ) Notice: Subject to any disclaimer, the term of this patent is extended or adjusted under 35 U.S.C. 154(b) by 348 days.

(21) Appl. No.: 12/344,279

(22) Filed: Dec. 25, 2008

(65) Prior Publication Data

US 2010/0162789 A1      Jul. 1, 2010

(51) Int. Cl.
*G01N 3/00* (2006.01)
(52) U.S. Cl. .................................................. 73/12.06
(58) Field of Classification Search ....... 73/12.01–12.09
See application file for complete search history.

(56) References Cited

U.S. PATENT DOCUMENTS

| | | | | |
|---|---|---|---|---|
| 4,910,995 A | * | 3/1990 | Nishio | 73/12.06 |
| 7,222,515 B2 | * | 5/2007 | Hatanaka et al. | 73/12.14 |
| 2008/0289395 A1 | * | 11/2008 | Torng et al. | 73/12.06 |

* cited by examiner

*Primary Examiner* — Lisa M Caputo
*Assistant Examiner* — Octavia Davis

(57) ABSTRACT

An apparatus for drop testing is disclosed. The apparatus has a drop angle setting jig that horizontally moves on a support frame and positions a test object at a predetermined angle by clamping with a fixture. The jig provides a second datum plane and is connected to a moveable holding frame, with the holding frame providing a first datum plane. After the fixture clamps the testing object, the jig can be pulled back without touching the testing object, and the testing object stays still. Therefore, the testing object can be precisely positioned. Furthermore, with the sliding track and the stopping block, the jig is able to quickly return back to the reference position.

14 Claims, 17 Drawing Sheets

APPARATUS FOR DROP TESTING AND METHOD UTILIZING THE SAME

BACKGROUND OF THE INVENTION

1. Field of the Invention

The present invention relates to the static or dynamic balance of a machine or device, and, more particularly, to an apparatus for drop testing and a method to utilize the same.

2. Description of the Related Art

In order to ensure products maintains their original quality in operational environments and during transportation, such as after the packaging process for packaged chip structure, some final quality tests such as aging tests, electrical tests, tensile tests, solder ball connection strength tests, etc., are performed to ensure quality and reliability. Subsequently, the packaged chip products are assembled into memory modules which can be utilized in standard electronic products, such as computers, mobile phones, digital cameras, PDAs, etc. Therefore, the requirements for impact and stress tolerances are higher and the related tests are more important. The packaging industry has established a strict testing standard, such as the drop test established by JEDEC, which can calculate the shock absorbing abilities of electronic products.

Some problems are present in the prior art drop test:

1. Low repeatability of the test: The prior art test requires manual positioning of the height and angle of the test object, which may lead to inconsistent drop angles and dropped surfaces and result in inconsistent results for each drop test.

2. High test costs and long preparation times: Since the test has low repeatability, numerous testers are required, and each different design requires new additional testers. Particularly during the product development period, each test has a high price, and drop testing is a destructive experiment so that repeating tests leads to high costs.

3. Impact might occur during the drop test, and the test object may undergo non-linear movement.

4. A prior art apparatus for drop testing can only execute a single test condition with fixed test parameters; for example, under a fixed height H, an impulse generated by the drop test. When there are different package type test objects or application environments, the prior art apparatus for drop testing does not support different drop test conditions. Since each manufacturer may have different drop test standards, each test condition requires a different apparatus for drop testing, which can lead to very high costs.

Therefore, it is desirable to provide an apparatus for drop testing to mitigate and/or obviate the aforementioned problems.

SUMMARY OF THE INVENTION

A main objective of the present invention is to provide an apparatus for drop testing that is suitable for different sized test objects, different drop angles and different testing conditions.

In order to achieve the above-mentioned objectives, an apparatus for drop testing of the present invention comprises: a support frame, a drop angle setting jig, and a fixture. The support frame has a sliding base, and the sliding base has a horizontal sliding rail. The drop angle setting jig is disposed on the sliding base and connected to a height adjustable sample holding frame. The sample holding frame provides a first datum plane, and the jig provides a second datum plane. The movement of the holding frame causes the first datum plane to move between a first predetermined position and a first pull-back position; when the jig horizontally moves with the guidance of the horizontal sliding rail, the second datum plane moves between a second predetermined position and a second pull-back position. When the fixture holds a test object, the first datum plane in the first predetermined position touches a first surface of the test object, and the second datum plane in the second predetermined position touches a second surface of the test object.

In an embodiment apparatus for drop testing, one edge of the sliding base has a first stopping block, and one edge of the drop angle setting jig has a second stopping block. When the second stopping block touches the first stopping block, the second datum plane moves to the second predetermined position.

In another embodiment apparatus for drop testing, the second stopping block has a securing element, which is used for securing the relative positioning between the jig and the sliding base.

In another embodiment apparatus for drop testing, the jig has an adjusting rod and an elastic element. The elastic element provides elastic strength for the holding frame to move towards the first predetermined position, and the adjusting rod limits the movement of the holding frame towards the first predetermined position.

In yet another embodiment apparatus for drop testing, both sides of the holding frame are connected to a sliding element, and both sides of the jig respectively have a vertical sliding rail for the sliding element to move vertically.

In an embodiment apparatus for drop testing, the bottom of the support frame has a plurality of adjusting feet for adjusting the horizontal level of the horizontal sliding rail.

In another embodiment apparatus for drop testing, the testing object is a long strip-shaped memory module.

In another embodiment apparatus for drop testing, the first datum plane and the second datum plane are perpendicular to each other.

The apparatus for drop testing may further comprise a clamping base that may be combined with the fixture.

In an embodiment apparatus for drop testing, the fixture has an opposite L shape and provides a first clamping face and a second clamping face. The clamping clearance of the first clamping face is smaller than the clamping clearance of the second clamping face and the first clamping face away from the first datum plane.

In another embodiment apparatus for drop testing, a gap is formed between the first datum plane in the first predetermined position and the second datum plane in the second predetermined position.

The present invention further provides a method of using an apparatus for drop testing. The method comprises: adjusting the holding frame and the jig such that the first datum plane is moved to the first predetermined position and the second datum plane is moved to the second predetermined position; placing a test object on the jig, a first surface of the test object touching the first datum plane, and a second surface of the test object touching the second datum plane; utilizing the fixture to fix the test object; lowering the holding frame such that the first datum plane is moved to the first pull-back position without touching the test object, but the test object continuing to touch the second datum plane of the jig; moving the jig horizontally such that the second datum plane is moved to the second pull-back position without touching the test object; and releasing the test object.

The apparatus for drop testing and its related method have the following benefits:

1. Suitability for different sized test objects and different drop surfaces.

2. Maintains the same height, angle and position during testing to increase test repeatability and reduce costs.

3. Quickly, precisely and securely controls the height, angle and position of the test object.

4. The sliding base is able to move without touching the test object and the test object does not move with the sliding base.

5. With the securing element and the stopping block, the drop angle setting jig can quickly and securely return back to the reference position.

6. With the adjusting feet, the holding frame of the drop testing apparatus can be maintained at a horizontal level so that the test object can drop straight down to provide correct measurement data.

7. Regardless of whether the test object is vertically standing or laying down at an angle for drop testing, it is not necessary to adjust the height of the fixture or the relative height of the clamping base.

Other objects, advantages, and novel features of the invention will become more apparent from the following detailed description when taken in conjunction with the accompanying drawings.

DETAILED DESCRIPTION OF THE PREFERRED EMBODIMENT

With reference to the attached drawings, the present invention is described by means of the embodiments below.

Figure 1:
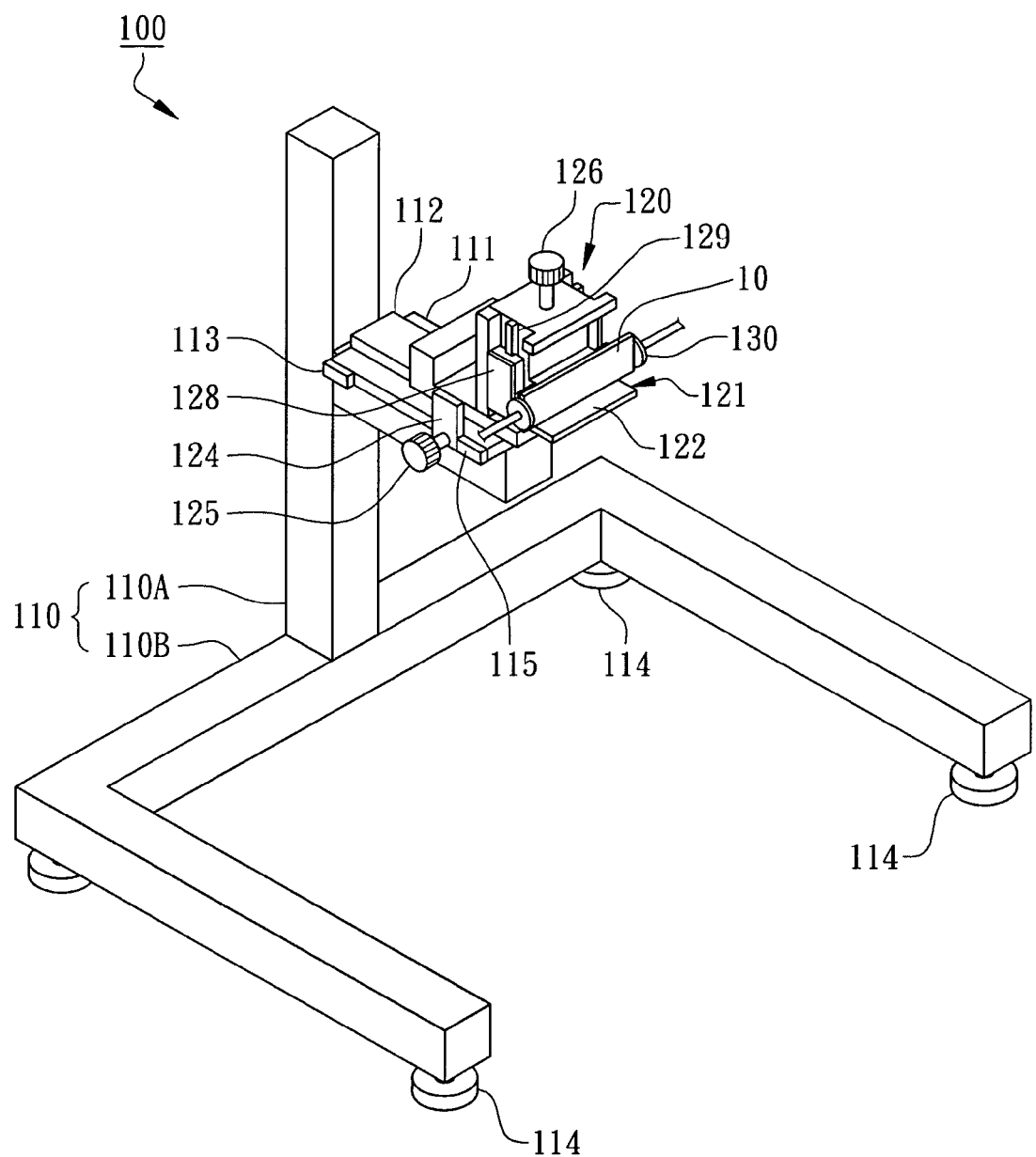
FIG. 1 is a perspective view of an apparatus for drop testing of a first embodiment according to the present invention.

According to a first embodiment of the present invention, an apparatus for drop testing is shown in FIG. 1. The apparatus 100 for drop testing comprises a support frame 110, a drop angle setting jig 120 and a fixture 130, and the apparatus 100 for drop testing is used for performing a drop test on a test object 10 to evaluate its shock resistance. The test object 10 can be a long strip-shaped memory module, such as a DIMM (Dual In-Line Memory Modules) or a SO-DIMM (Small Outline Dual In-Line Memory Modules). The test object 10 can also be other electronic devices, or flip chip packaged structures, lead-frame packaged structures, multi-chip packaged structures or other typical packaging structures. Since there are various chip packaging types, each manufacturer may have its own testing standards, and the adjustable apparatus for drop testing of the present invention provides different test conditions to reduce testing costs.

Figure 2:
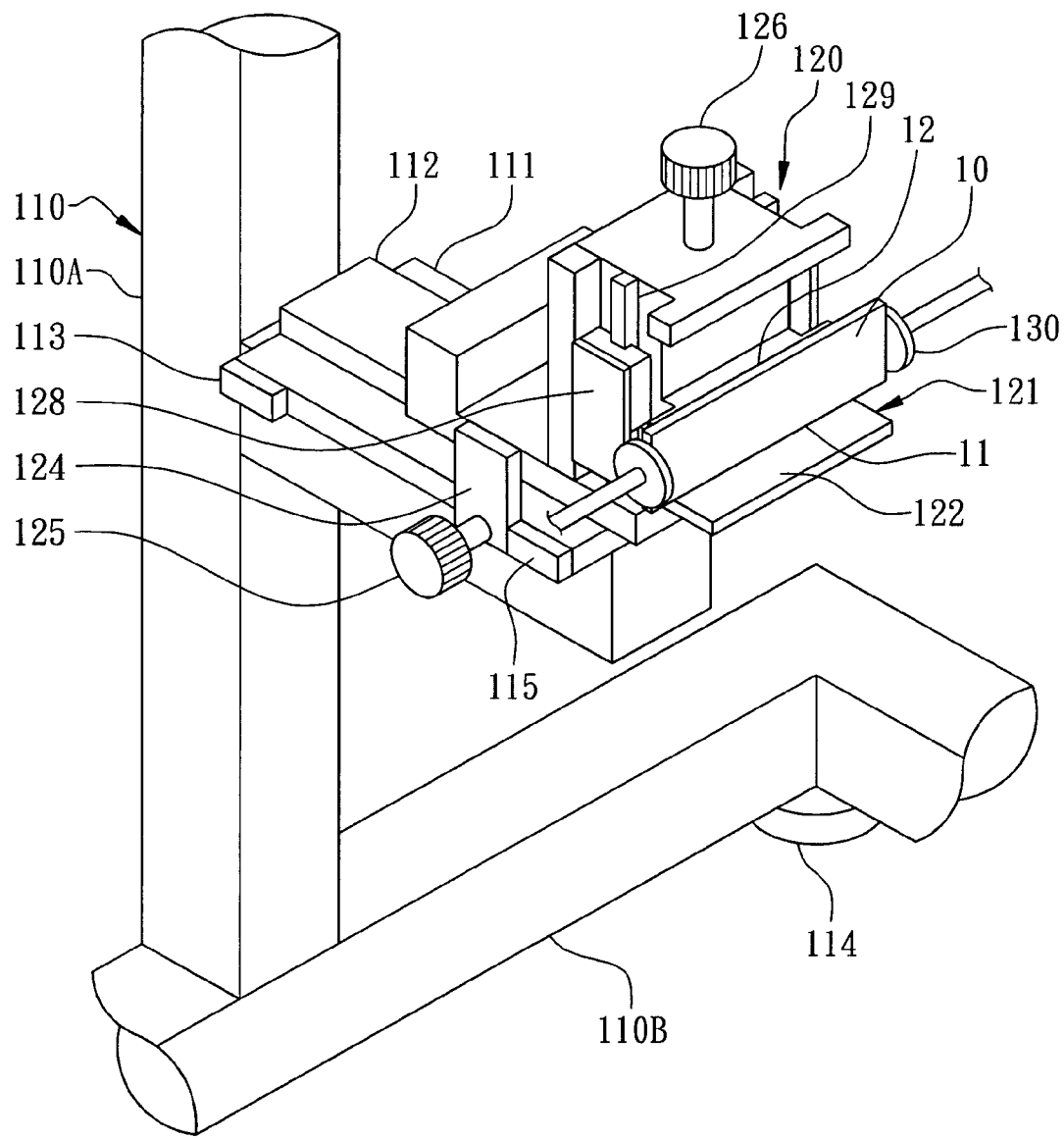
FIG. 2 is a detailed perspective view of a drop angle setting jig of the apparatus for drop test holding of a test object and being moved to a predetermined position according to the first embodiment of the present invention.

Please refer to FIGS. 1 and 2. The support frame 110 comprises a sliding base 111, and the sliding base 111 has a horizontal sliding rail 112. The support frame 110 is composed of a vertical frame 110A and a bottom frame 110B. The vertical frame 110A is vertically installed on the bottom frame 110B, and the bottom frame 110B of the support frame 110 occupies a relatively large area to stabilize the support frame 110. In this embodiment, the bottom frame 110B has an upside down U shape which surrounds an area for drop testing (as shown in FIG. 1). The sliding base 111 is disposed on a cantilever of the support frame 110 at a predetermined height, such as 30 cm, 50 cm, 60 cm or even 120 cm, to provide different heights for the drop angle setting jig 120.

Figure 3:
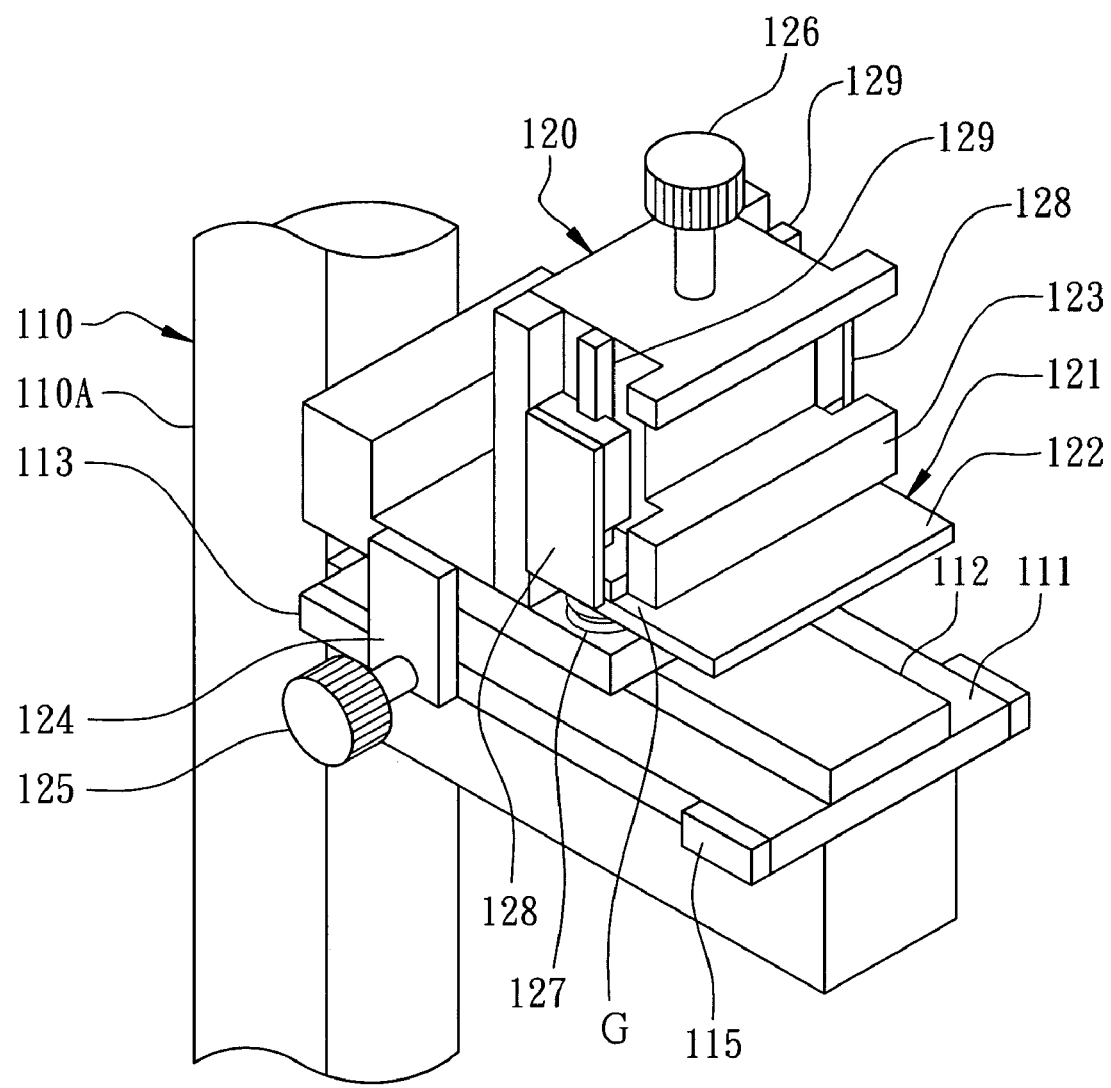
FIG. 3 is a detailed view of the drop angle setting jig of the apparatus for drop test holding of the test object and being moved to a pull-back position according to the first embodiment of the present invention.

As shown in FIGS. 2 and 3, the drop angle setting jig 120 is disposed on the sliding base 111 and connected to a moveable holding frame 121 (as shown in FIG. 3), and the holding frame 121 provides a first datum plane 122 that can be horizontal or inclined. The jig 120 provides a second datum plane 123 that can be vertical or inclined. The jig 120 can be guided by the horizontal sliding rail 112 for horizontal movement. Preferably, the first datum plane 122 and the second datum plane 123 are perpendicular to each other and used for positioning of the test object.

Figure 5A:
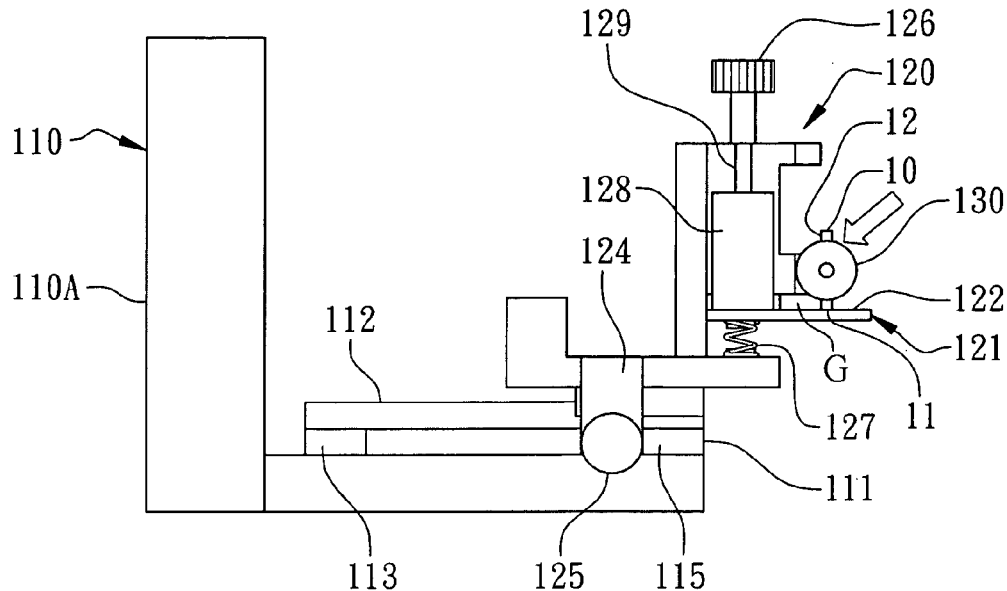
FIGS. 5A to 5F are side views of the apparatus for drop testing according to the first embodiment of the present invention.
Figure 5B:
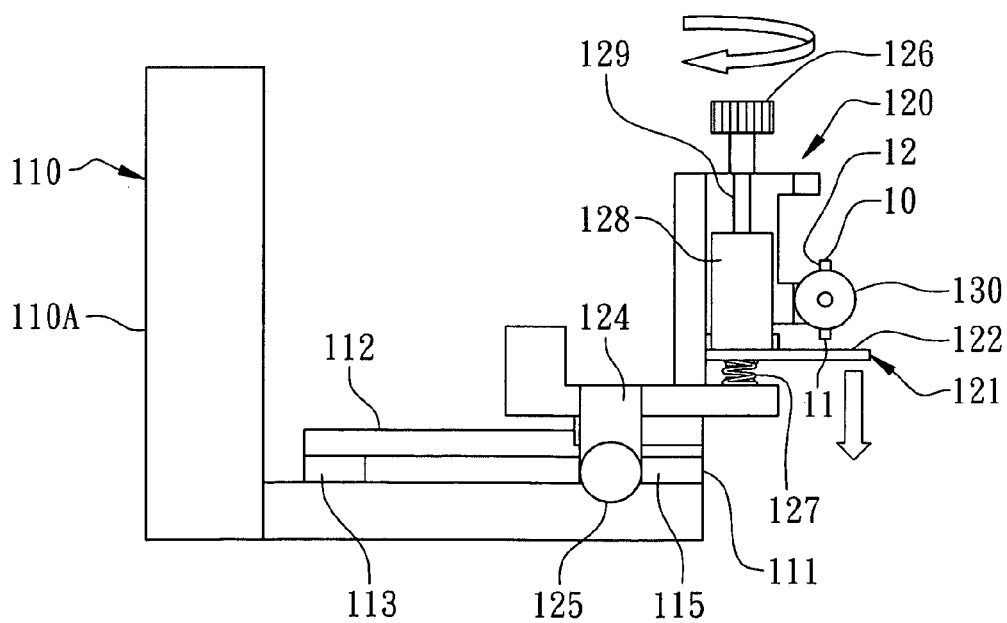

Movement of the holding frame 121 causes the first datum plane 122 to move between a first predetermined position and a first pull-back position. The first predetermined position is an upper position for the holding frame 121 (as shown in FIG. 5A), and the first pull-back position is a lower position for the holding frame 121 (as shown in FIG. 5B).

Figure 5C:
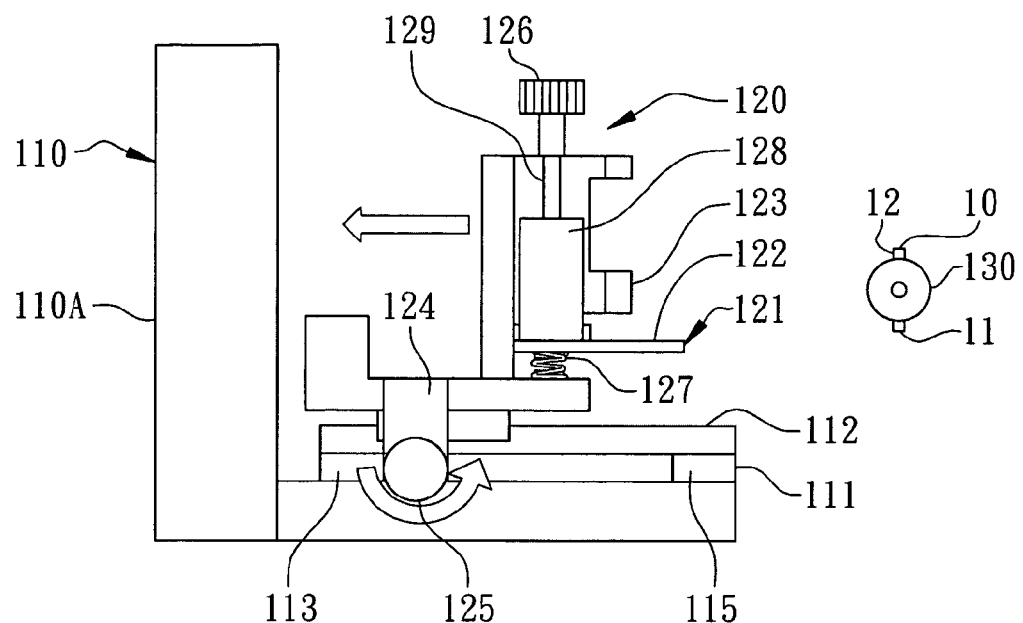
Figure 5D:
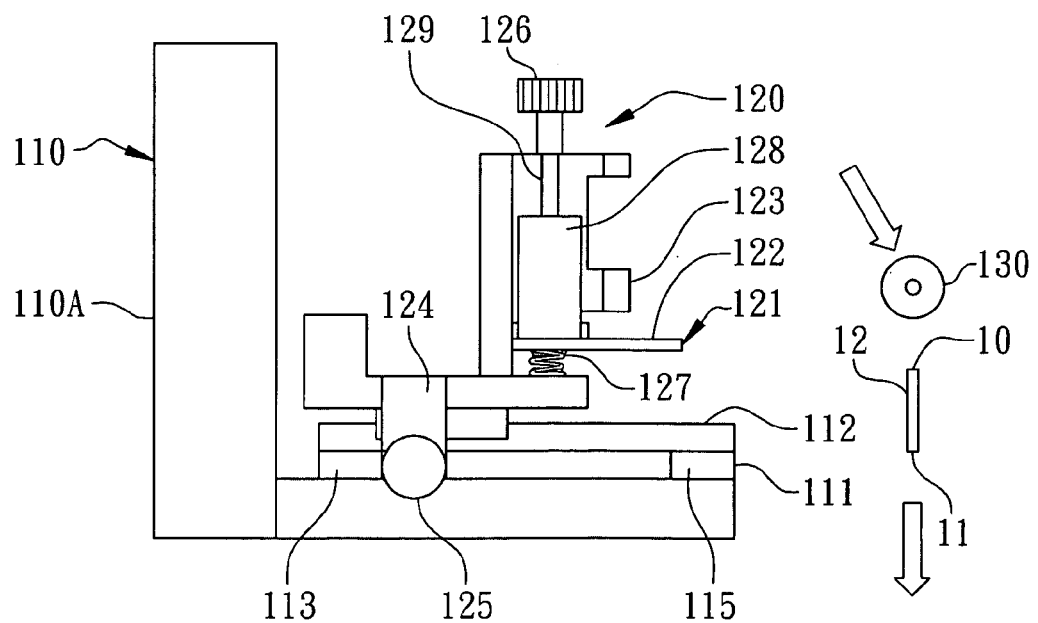

When the jig 120, guided by the horizontal sliding rail 112, undergoes horizontal movement, the second datum plane 123 moves between a second predetermined position and a second pull-back position. The second predetermined position is a position at which the second datum plane 123 moves forward away from the support frame 110 (as shown in FIGS. 5A and 5B), and the second pull-back position is a position at which the second datum plane 123 moves backward towards the support frame 110 (as shown in FIG. 5D).

As shown in FIG. 2, when the fixture 130 clamps the test object 10, a first surface 11 of the test object 10 touches the first datum plane 122 in the first predetermined position. In other words, the testing object 10 is placed on the holding frame 121, and a second surface 12 of the testing object 10 touches the second datum plane 123 in the second predetermined position (as shown in FIGS. 2 and 3). In this embodiment, the first surface 11 is the long side surface of the memory module, and the second surface 12 is the substrate surface of the memory module or the component assembly surface.

After placement of the test object 10, the first surface 11 and the second surface 12 of the test object 10 touch the first datum plane 122 and the second datum plane 123, and the fixture 130 clamps the both sides of the test object 10. In this embodiment, the clamped surfaces of the test object 10 are the short side surfaces of the memory module. Therefore, it is very easy to precisely place and maintain the test object 10 at a test height, test angle and test position without shifting. The two ends of the fixture 130 (not shown) are connected to the vertical frame 110A, and fixture 130 may be set at different heights. Furthermore, the fixture 130 is flexible for different sizes of test objects 10.

As shown in FIGS. 2 and 3, one edge of the sliding base 111 has a first stopping block 113, and one edge of the drop angle setting jig 120 has a second stopping block 124. The edge of the sliding base 111 and the edge of the drop angle setting jig 120 are on the same side so that when the drop angle setting jig 120 is moved horizontally backward, the second stopping block 124 touches the first stopping block 113, which causes the second datum plane 123 to move to the second pull-back position (as shown in FIGS. 3 and 5D). Furthermore, the edge of the sliding base 111 further includes a third stopping block 115. When the drop angle setting jig 120 is moved forward horizontally, the second stopping block 124 touches the third stopping block 115, which causes the second datum plane 123 to move to the second predetermined position. As a result, the second predetermined position and the second pull-back position are clearly defined.

In addition, as shown in FIG. 2, the second stopping block 124 further includes a securing element 125, which is used for securing the relative positioning between the jig 120 and the sliding base 111.

As shown in FIG. 3, the jig 120 has an adjusting rod 126 and an elastic element 127. The elastic element 127 provides elastic strength for the holding frame 121 for movement towards the first predetermined position, and the adjusting rod 126 limits movement of the holding frame 121 toward the first predetermined position. With the adjusting rod 126 and the elastic element 127, the first datum plane 122 of the holding frame 121 can precisely reach the first predetermined position. With the adjusting rod 126 and the elastic element 127, the first datum plane 122 of the holding frame 121 can also precisely reach the first pull-back position. Therefore, the first predetermined position and the first pull-back position are clearly defined. Additionally, two sides of the holding frame 121 are respectively connected to a sliding element 128, and two sides of the jig 120 respectively have a vertical sliding rail 129 for the sliding element 128 to vertically move thereon. With rotation of the adjusting rod 126, the holding frame 121 is guided along the vertical sliding rail 129 for vertical movement.

Figure 4:
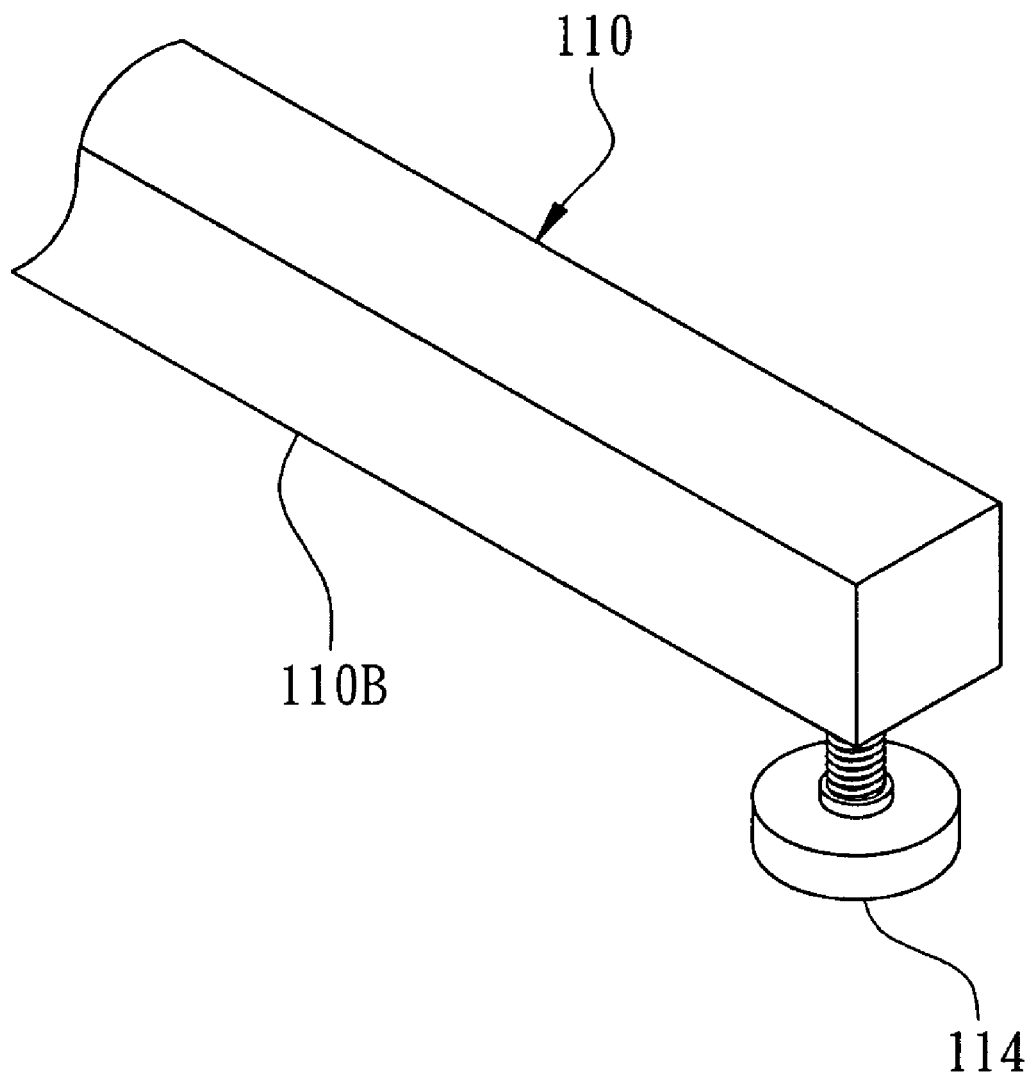
FIG. 4 is a perspective view of adjusting feet of the apparatus for drop testing according to the first embodiment of the present invention.

By way of a more detailed description, as shown in FIGS. 1 and 4, the bottom of the support frame 110 has a plurality of adjusting feet 114, and the adjusting feet 114 are located at two or four corners of the bottom frame 110B of the support frame 110 and used to adjust the horizontal level of the horizontal sliding rail 112 to ensure the horizontal positioning of the holding frame 121 of the apparatus 100 for drop testing so that the test object 20 can be dropped vertically and accurate data can be measured.

The following description explains the operation of the apparatus 100 for drop testing. Please refer to FIG. 5A to FIG. F.

At first, as shown in FIG. 5A, the holding frame 121 and the jig 120 are adjusted to cause the first datum plane 122 to move to the first predetermined position and the second datum plane 123 to move to the second predetermined position. The first predetermined position is an upper position for the first datum plane 122 of the holding frame 121, and the second predetermined position is a front position for the second datum plane 123. The second datum plane 123 and the first datum plane 122 compose a 90° angle. Next, as the arrow shows in FIG. 5A, a test object 10 is placed on the holding frame 121 of the jig 120; the first surface 11 of the test object 10 touches the first datum plane 122, and the second surface 12 of the test object 10 touches the second datum plane 123 (as shown in FIG. 5C). Subsequently, the fixture 130 clamps two sides of the test object 10 (as shown in FIG. 2) to stabilize and precisely control and maintain the height and angle of the test object 10 without shifting.

As shown in FIG. 5B, by rotating the adjusting rod 126 to lower the holding frame 121, the first datum plane 122 moves to the first pull-back position and does not touch the first surface 11 of the test object 10, but the second surface 12 of the test object 10 continues to touch the second datum plane 123 of the jig 120. A clockwise rotational direction of the adjusting rod 126 is shown by an arrow in FIG. 5B. The lowering direction is indicated by another arrow shown in FIG. 5B.

As shown in FIG. 5C, the jig 120 is horizontally moved so that the second datum plane 123 moves to the second pull-back position and does not touch the test object 10. The horizontal direction of movement is indicated by the left pointing arrow shown in FIG. 5C. When the second stopping block 124 touches the first stopping block 113, the securing element 125 secures the relative position between the jig 120 and the sliding base 111 and allows no relative sliding. The securing element 125 may be rotated in a counterclockwise direction as shown in FIG. 5C. When the jig 120 is moved horizontally backward, since the first surface 11 of the test object 10 does not touch the first datum plane 122, the sliding base 111 moves without resistance between the test object 10 and the test object 10 is not moved by the movement of the sliding base 111. The test object 10 is clamped by the fixture 130 along its two sides and held suspended.

As indicated by the arrow in FIG. 5D, the fixture 130 releases the test object 10 to drop to the ground, and the first surface 11 faces downward. The direction of dropping is shown by the downward arrow in FIG. 5D.

Figure 5E:
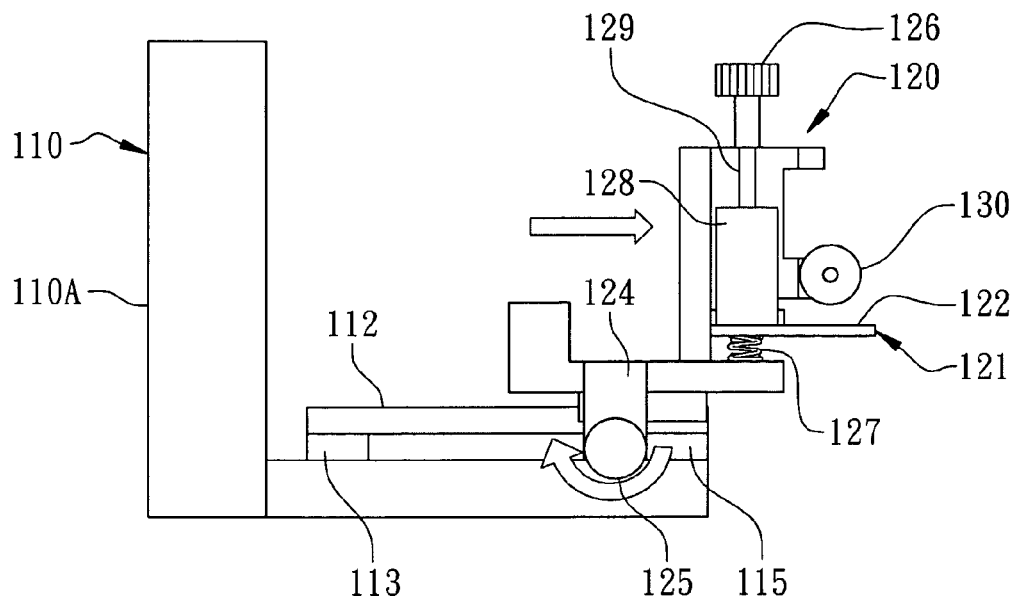

For the next test object 10, as shown in FIG. 5E, the jig 120 is horizontally moved back to the second predetermined position. The horizontal movement is shown by the rightward pointing arrow in FIG. 5E. Subsequently, the second stopping block 124 touches the third stopping block 115, and the jig 120 is stopped from moving. The securing element 125 secures the relative position between the jig 120 and the sliding base 111 so that they don't slide relative to each other. The securing method is performed by rotating the securing element 125 in a clockwise direction as shown by the arrow in FIG. 5E.

Figure 5F:
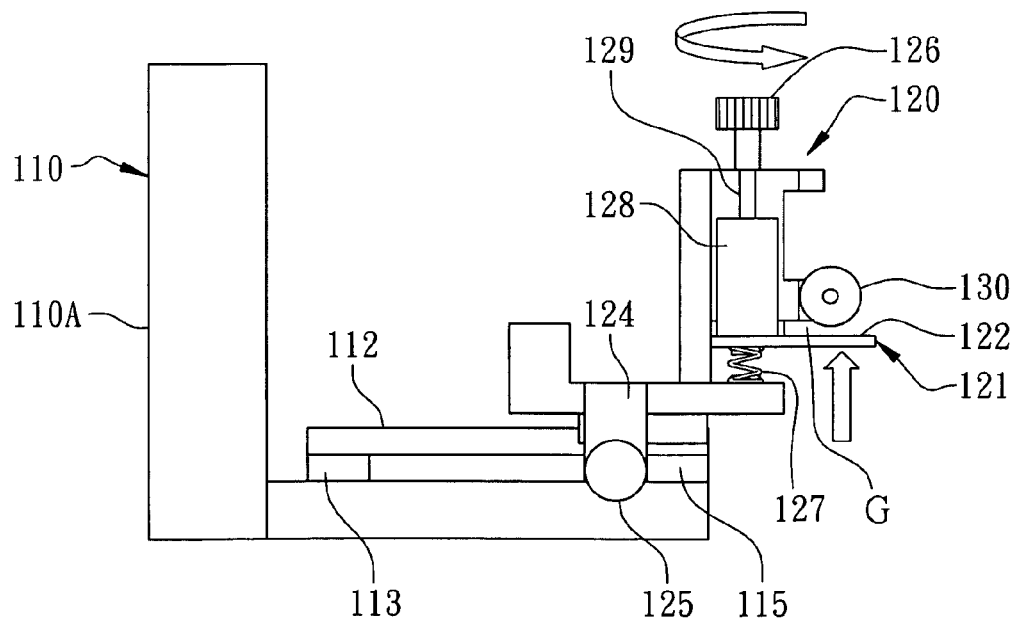

As shown in FIG. 5F, the adjusting rod 126 is rotated to raise the first datum plane 122 of the holding frame 121 back to the first predetermined position (which is the predetermined testing height). The above-mentioned rotational direction of the adjusting rod 126 is shown by the arrow in FIG. 5F, and the raising direction of the first datum plane 122 is shown by the upward pointing arrow in FIG. 5F.

Subsequently, the steps shown in FIGS. 5A to 5F are repeated, in order to repeatedly test the test object 10. During the testing process, the test object 10 is maintained at the same drop height and position but at different initial drop angles, and the repeatability and accuracy of testing is increased to reduce test-related cost.

Figure 6:
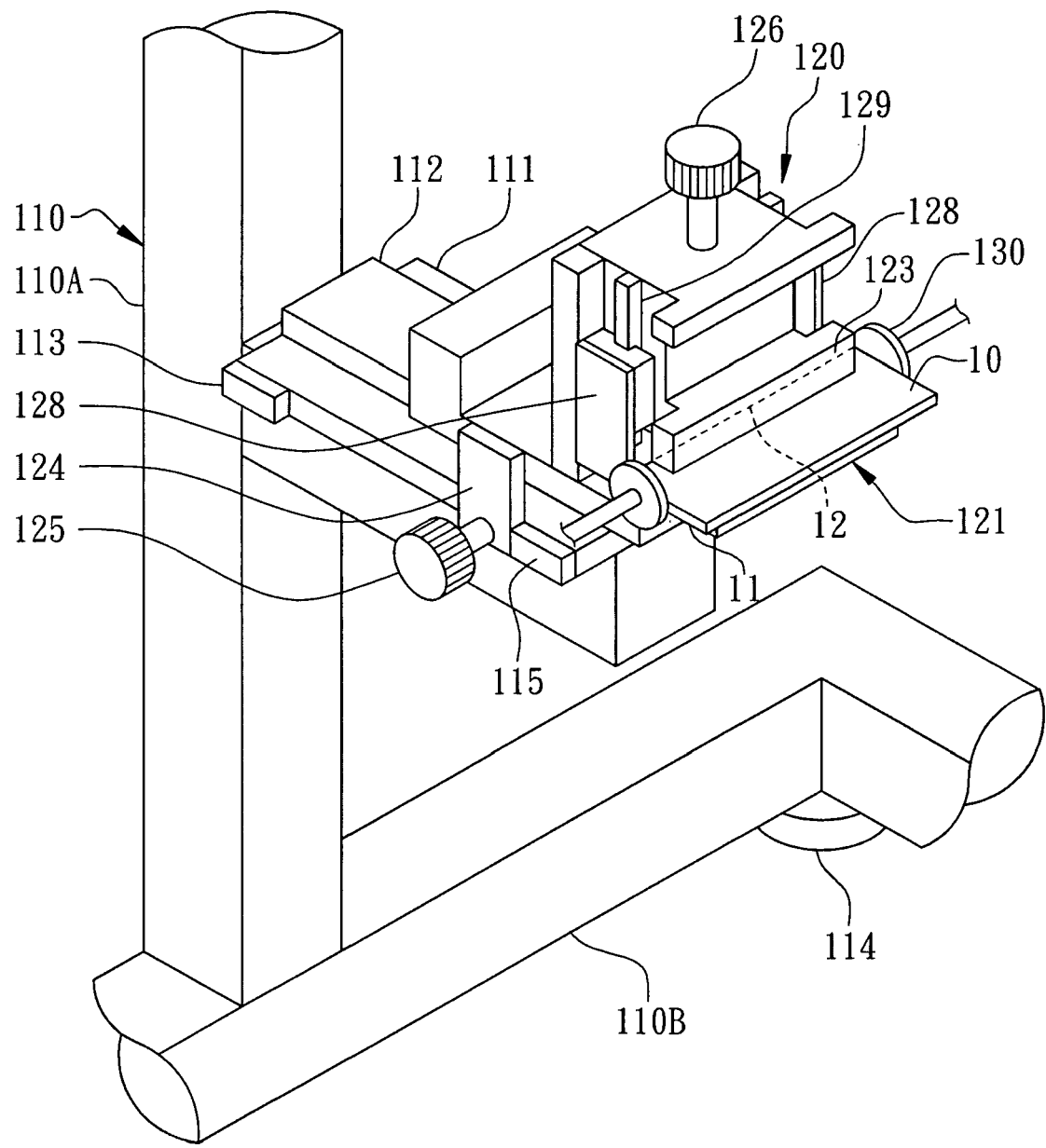
FIG. 6 is a detailed view of the drop angle setting jig being moved to the predetermined position and holding the test object at a second adjustable drop angle according to the first embodiment of the present invention.

The apparatus 100 for drop testing can provide different initial drop angles for different sized test objects 10. As shown in FIG. 6, the test object 10 can be laid width-wise on the holding frame 121. As shown in FIGS. 3 and 5F, a gap G exists between the first datum plane 122 in the first predetermined position and the second datum plane 123 in the second predetermined position, with the gap G having bigger than or equal to the width of the test object 10. When the test object 10 is laid width-wise, a portion of the test object 10 can be pushed into to the gap G without adjusting the height of the fixture 130. Subsequently, the first surface 11 of the test object 10 touching the first datum plane 122 is the substrate surface of the memory module or the component assembly surface, and the test object 10 is placed on the holding frame 121. The second surface 12 of the test object 10 is the long side surface of the memory module, which is partially inserted in the gap G between the second datum plane 123 and the holding frame 121. Therefore, the fixture 130 clamps onto the short side surfaces of the memory module.

Figure 7:
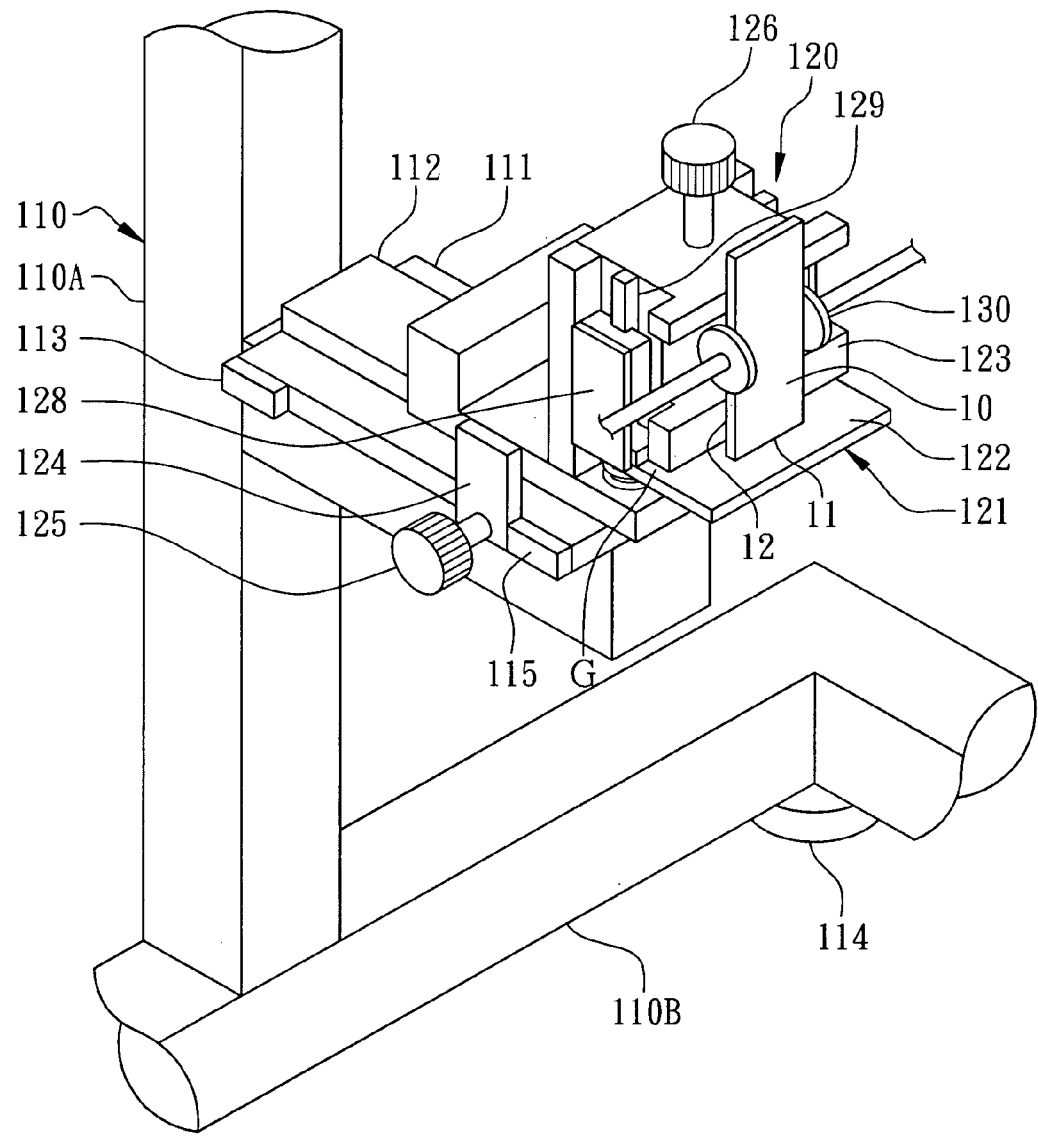
FIG. 7 is a detailed perspective view of the drop angle setting jig being moved to the predetermined position and holding the test object at a third adjustable drop angle according to the first embodiment of the present invention.

Alternatively, as shown in FIG. 7, the test object 10 can also be vertically positioned on the holding frame 121. The first surface 11 of the testing object 10 touches the first datum plane 122, and the second surface 12 of the testing object 10 touches the second datum plane 123. The first surface 11 of the testing object 10 is the short side surface of the memory module, and the second surface 12 of the testing object 10 is the substrate surface of the memory module or the component assembly surface. Therefore, the fixture 130 clamps on the long side surfaces of the memory module.

Figure 8:
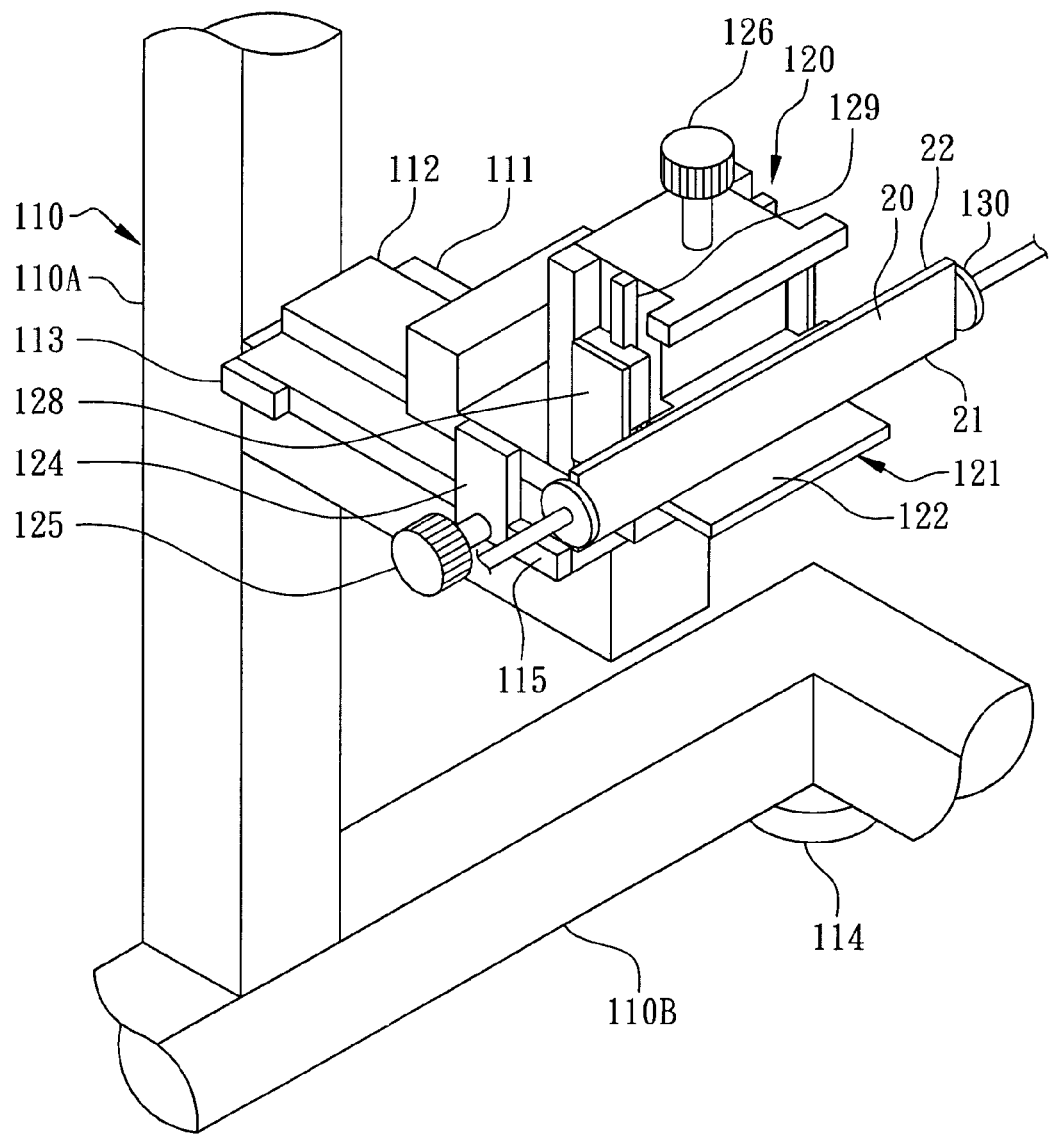
FIG. 8 is a detailed perspective view of the drop angle setting jig of the apparatus for drop testing being moved to the predetermined position and holding another testing object.

Moreover, as shown in FIG. 8, the apparatus 100 for drop testing can also accept a test object 20 having different sizes or which is of a different product type. A first surface 21 of the test object 20 touches the first datum plane 122, and a second surface 22 of the test object 20 touches the second datum plane 123 (as shown in FIG. 7). The clamping clearance of the fixture 130 can be adjusted for different sized test objects 20 so the apparatus 100 for drop testing can perform drop tests on test objects having different sizes.

Figure 9:
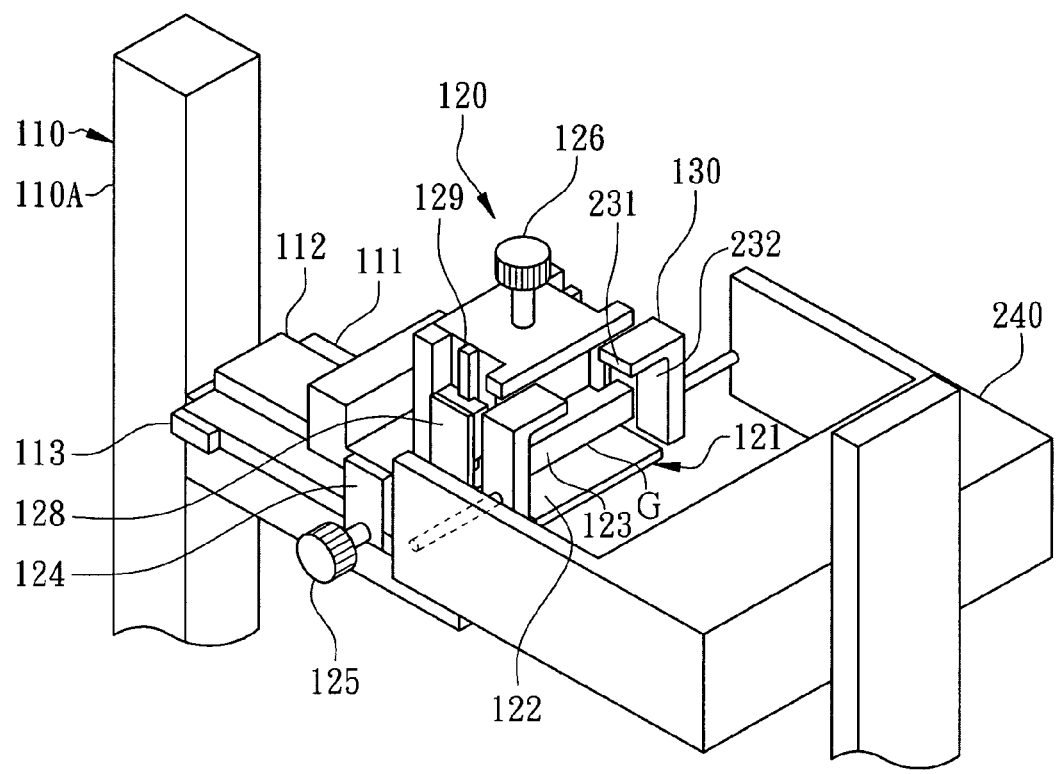
FIG. 9 is a detailed perspective view of an apparatus for drop testing according to a second embodiment of the present invention.

According to a second embodiment of the present invention, another apparatus for drop testing is shown in FIG. 9. The apparatus for drop testing comprises a support frame 110, a drop angle setting jig 120 and a fixture 130; wherein identical elements with identical functionality or effects as those in the first embodiment are marked with the identical numbers with no further description.

In this embodiment, the apparatus for drop testing further comprises a clamping base 240, which is used in combination with the fixture 130. The clamping base 240 can be placed facing the support frame 110 and be combined with the fixture 130 with a connecting horizontal rod. The fixture 130 has an upside-down L shape, which provides a first clamping face 231 and a second clamping face 232. The clamping clearance of the first clamping face 231 is smaller than the clamping clearance of the second clamping face 232. The first clamping face 231 is spaced relatively away from the first datum plane 122; therefore, when drop tests with different drop angles are performed, there is no need to adjust the height of the fixture 130 and the clamping base 240 without moving the clamping base 240. When the horizontal distance difference of the first clamping face 231 and the second clamping face 232 of the fixture 130 is equal to half of the length difference between the long side surface and the short side surface of the test object 10, the fixture 130 can use the same clamp stroke to set the test object 10 into a vertical standing position, a horizontal position, or a transverse horizontal position.

Figure 10A:
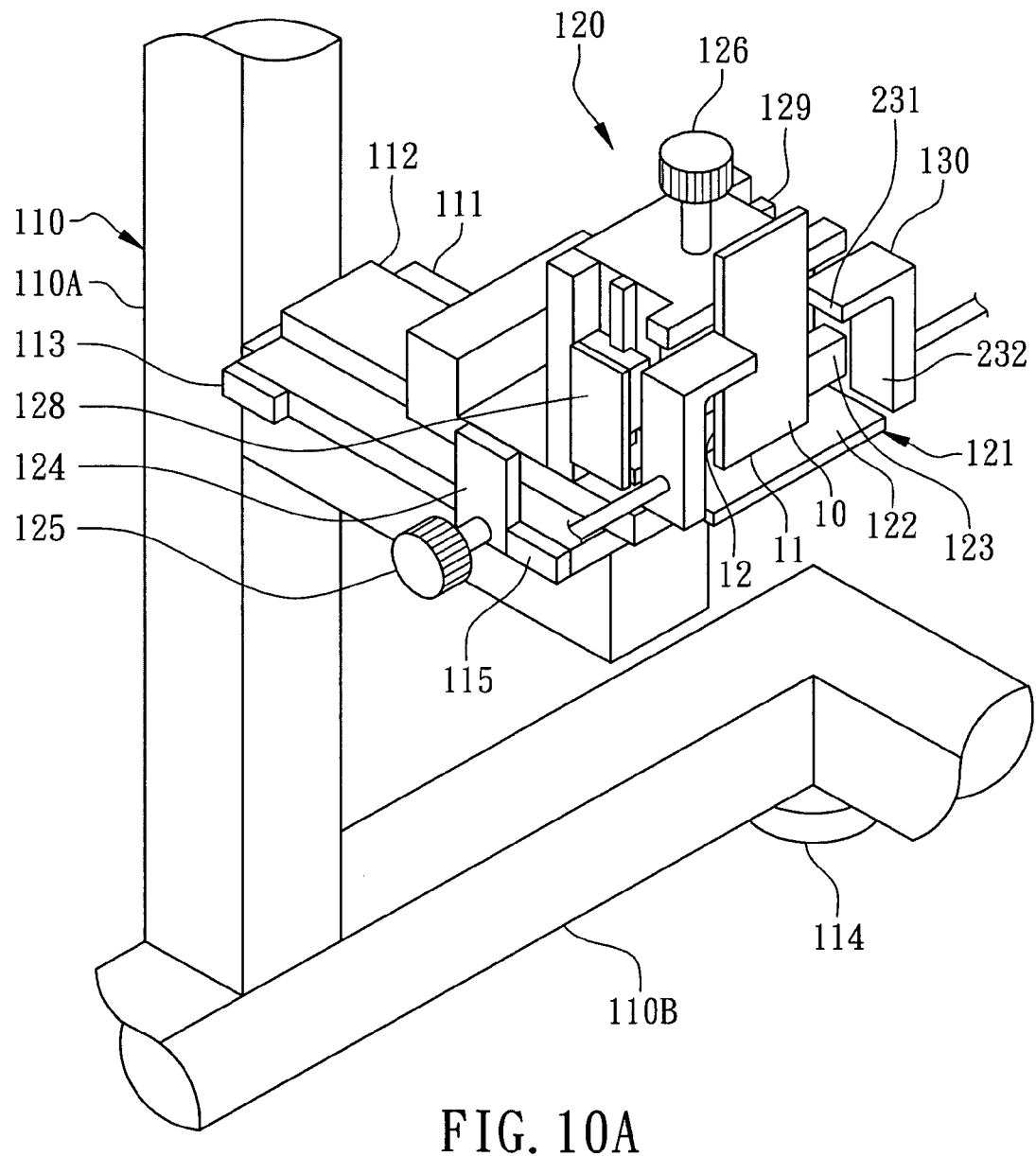
FIGS. 10A to 10C are detailed perspective views of the drop angle setting jig being moved to the predetermined position and holding the test object at different drop angles such as vertical, horizontal, and transverse horizontal according to the second embodiment of the present invention.
Figure 10B:
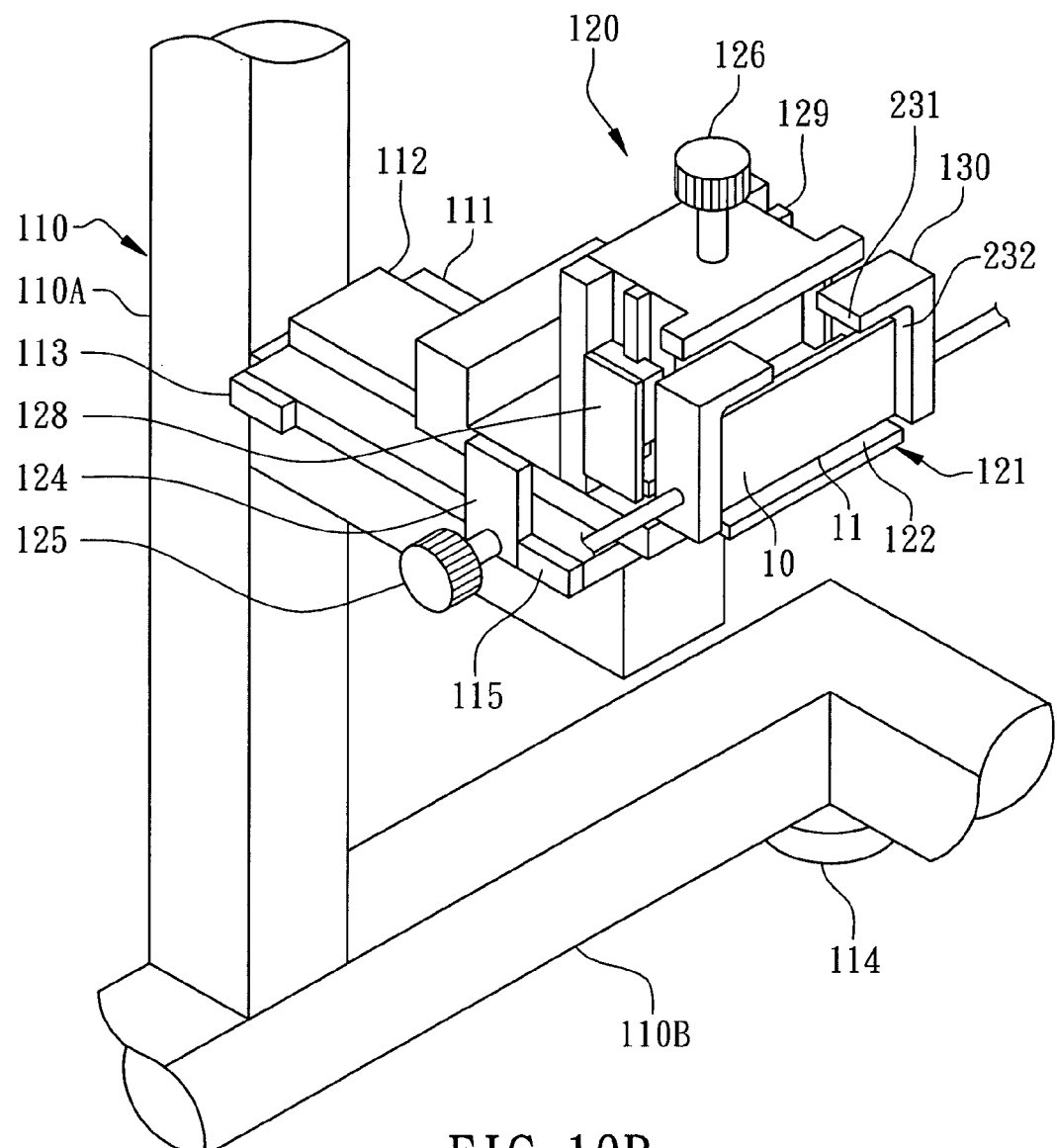
Figure 10C:
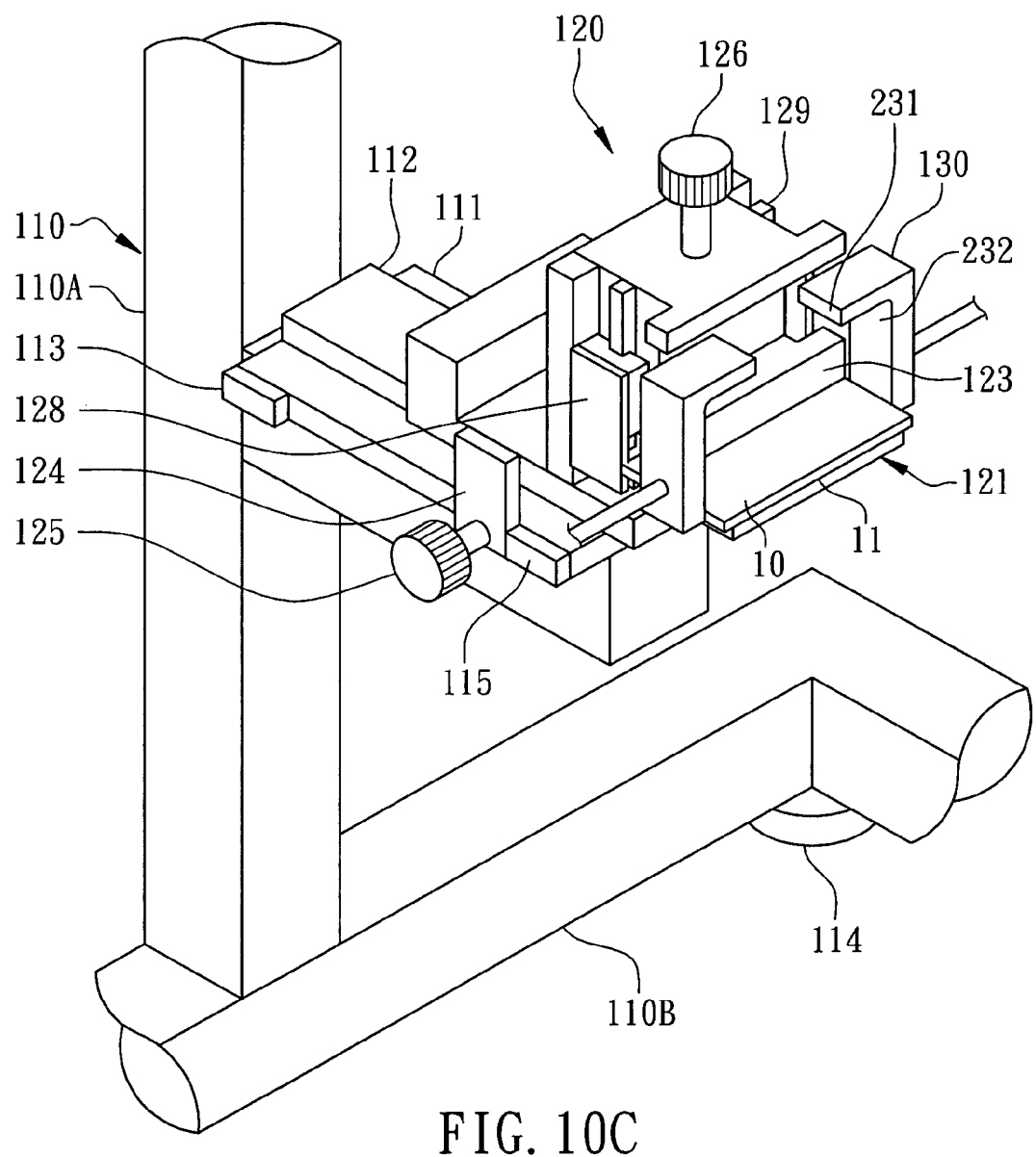

Drop tests with different drop angles are shown in FIGS. 10A to 10C. As shown in FIG. 10A, when the test object 10 is in a vertical standing position on the holding frame 121, the first surface 11 of the test object 10 touches the first datum plane 122, and the second surface 12 of the test object 10 touches the second datum plane 123. The first surface 11 is the short side surface of the memory module, and the second surface 12 is the substrate surface of the memory module or the component assembly surface. The clamping clearance of the first clamping face 231 of the fixture 130 is adjusted to be equal to the length of the short side surface of the memory module so that the first clamping face 231 of the fixture 130 can clamp onto center position of the long side surface of the memory module without adjusting the height of the fixture 130.

When the test object 10 is in horizontal position on the holding frame 121 (as shown in FIG. 10B), the first surface 11 of the test object 10 touches the first datum plane 122, and the second surface of the test object 10 touches the second datum plane. The first surface 11 is the long side surface of the memory module, and the second surface 12 is the substrate surface of the memory module or the component assembly surface. The clamping clearance of the second clamping face 232 of the fixture 130 is adjusted to be equal to the length of the long side surface of the memory module so that the second clamping face 232 of the fixture 130 can clamp onto the short side surface of the memory module.

When the test object 10 is in a transverse horizontal position on the holding frame 121 (as shown in FIG. 10C), a portion of the test object 10 can be pushed into the gap G without adjusting the height of the fixture 130. The first surface 11 of the test object 10 touching the first datum plane 122 is the substrate surface of the memory module or the component assembly surface, and the test object 10 is placed on the holding frame 121. One of the long side surfaces of the testing object 10 is partially inserted into the gap G between the second datum plane 123 and the holding frame 121. Therefore, the fixture 130 clamps onto the short side surfaces of the memory module.

Therefore, whether the testing object 10 is in a vertical standing position, a horizontal position, or a transverse horizontal position for the drop testing, the heights of the fixture 130 and the clamping base 240 do not need to be adjusted, and the drop testing can be performed to the same type of testing object 10 at different drop angles (including a vertical standing position, a horizontal position, or a transverse horizontal position). With a difference between the clamping clearance of the first clamping face 231 and the clamping clearance of the second clamping face 232, the testing object 10 can be positioned at the same vertical standing position, the same horizontal position, or the same transverse horizontal position.

Figure 11A:
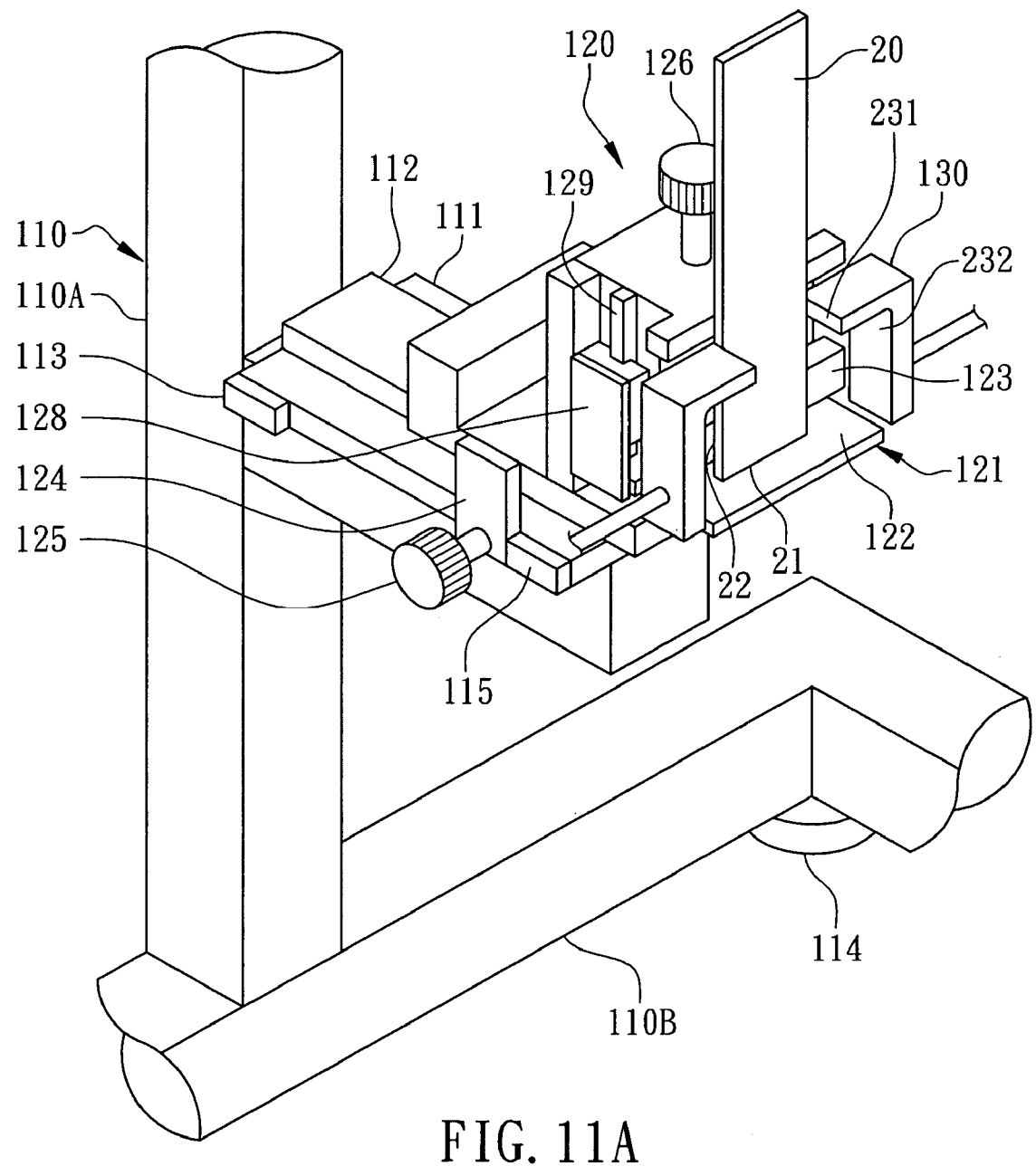
FIGS. 11A to 11C show detailed perspective views of the drop angle setting jig being moved to the predetermined position and holding the test object at different drop angles such as vertical, horizontal, and transverse horizontal according to the second embodiment of the present invention.
Figure 11B:
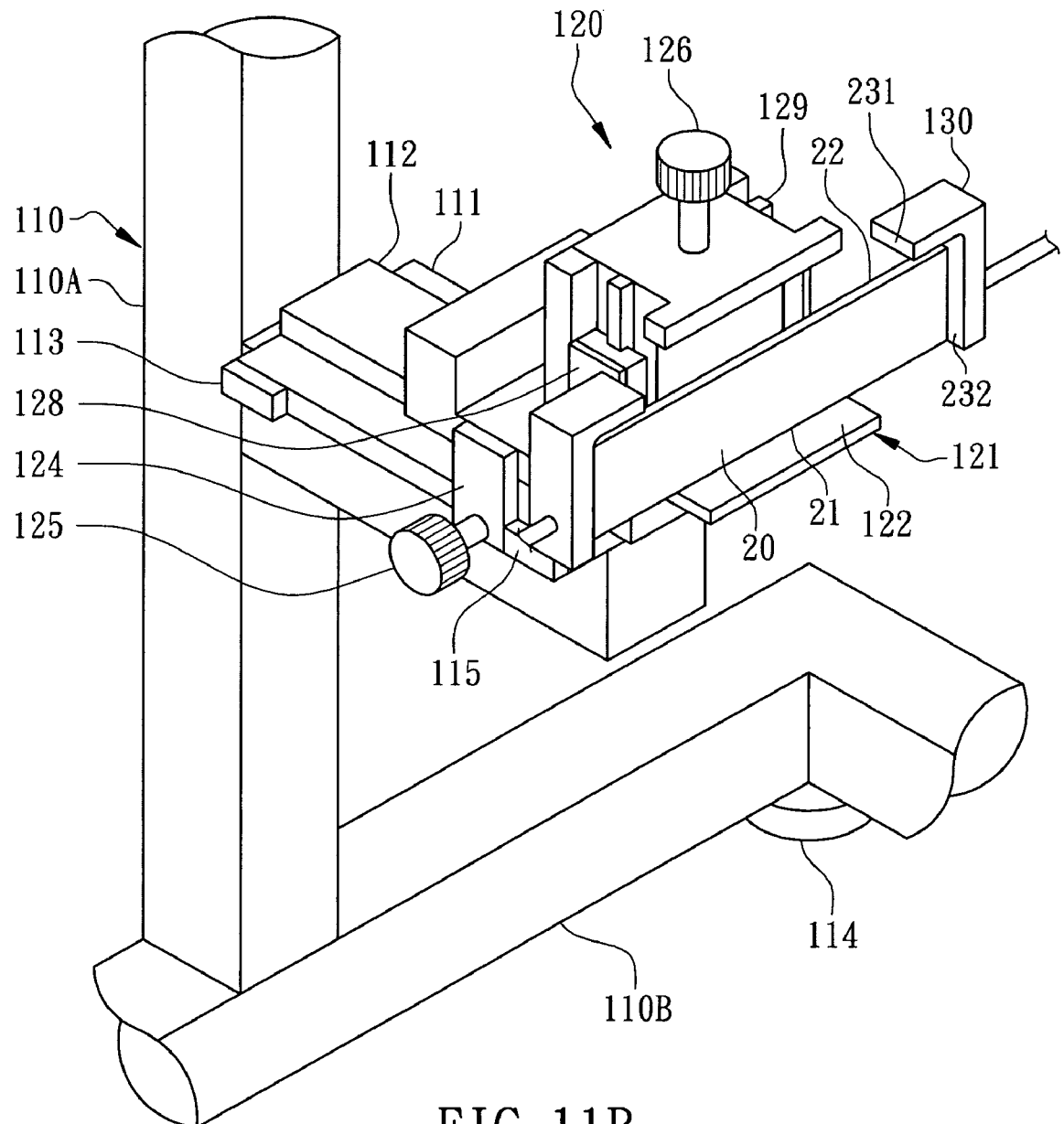
Figure 11C:
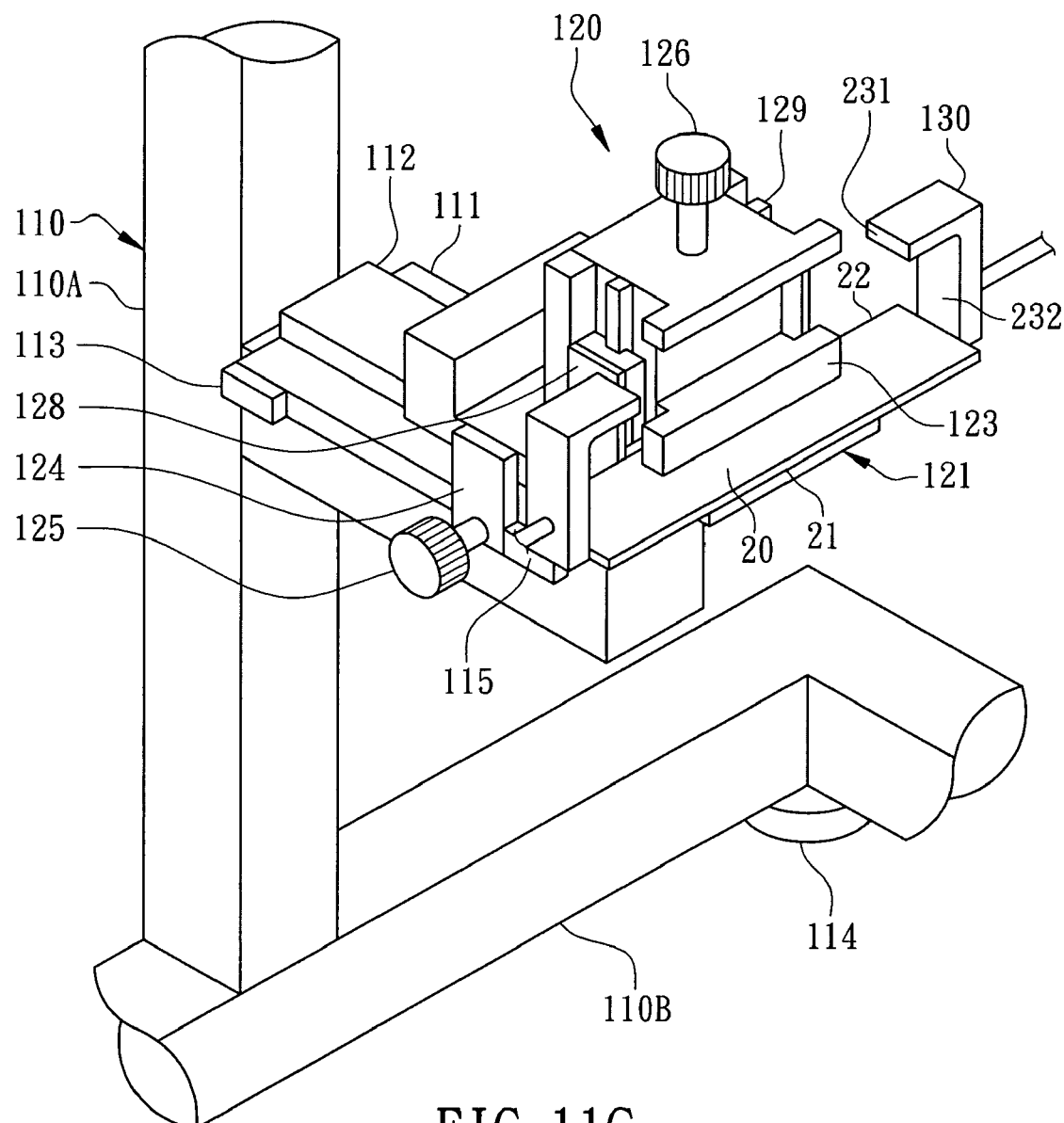

As shown in FIGS. 11A to 11C, the apparatus for drop testing can also accept the test object 20 having different sizes or which is of a different product type. The test object 20 can be much longer or bigger than the above-mentioned test object 10. The fixture 130 has an upside-down L shape, which provides a first clamping face 231 and a second clamping face 232. As shown in FIG. 11A, the test object 20 may be in the vertical standing position on the holding frame 121. The test object 20 touches the first surface 21 of the first datum plane 122 which is the short side surface of the memory module; and the test object 20 touches the second surface 22 of the second datum plane 123 which is the substrate surface of the memory module or the component assembly surface. Subsequently, the first clamping face 231 of the fixture 130 is able to clamp onto the long side surface of the memory module for drop testing in the vertical standing position.

As shown in FIG. 11B, the test object 20 may be in a horizontal position on the holding frame 121. The test object 20 touches the first surface 21 of the first datum plane 122 is the long side surface of the memory module; and the test object 20 touches the second surface 22 of the second datum plane 123 with the substrate surface of the memory module or the component assembly surface. Subsequently, the second clamping face 232 of the fixture 130 is able to clamp onto the short side surface of the memory module for drop testing in the horizontal position.

As shown in FIG. 11C, the test object 20 may be in a transverse horizontal position on the holding frame 121. The test object 20 touches the first surface 21 of the first datum plane which is the substrate surface of the memory module or the component assembly surface, the second surface 22 of the test object 20 is partially inserted into the gasp G (as shown in FIG. 9), and the second surface 22 is the long side surface of the memory module. Subsequently, the second clamping face 232 of the fixture 130 is able to clamp onto the short side surface of the memory module for drop testing in the transverse horizontal position.

As a result, the same type of test object 20 can be tested with different drop angles, such as the vertical standing position, the horizontal position, or the transverse horizontal position, and there is no need to adjust the heights of the fixture 130 and the clamping base 240. With the drop angle setting jig 120 of the apparatus for drop testing and its combination, testing conditions have good reproducibility without manual configuration errors.

Although the present invention has been explained in relation to its preferred embodiments, it is to be understood that many other possible modifications and variations can be made without departing from the spirit and scope of the invention as hereinafter claimed.

What is claimed is:

1. An apparatus for drop testing comprising:
    a support frame having a sliding base, the sliding base having a horizontal sliding rail;
    a drop angle setting jig disposed on the sliding base and connected to a height adjustable sample holding frame, the sample holding frame providing a first datum plane, and the jig providing a second datum plane; wherein movement of the holding frame causes the first datum plane to move between a first predetermined position and a first pull-back position, and when the jig horizontally moves with the guidance of the horizontal sliding rail, the second datum plane moves between a second predetermined position and a second pull-back position; and
    a fixture, wherein when the fixture holds a testing object, the first datum plane in the first predetermined position touches a first surface of the test object, and the second datum plane in the second predetermined position touches a second surface of the test object.

2. The apparatus for drop testing as claimed in claim 1, wherein an edge of the sliding base has a first stopping block, and an edge of the drop angle setting jig has a second stopping block, and when the second stopping block touches the first stopping block, the second datum plane moves to the second predetermined position.

3. The apparatus for drop testing as claimed in claim 2, wherein the second stopping block has a securing element that is used for securing a relative position between the jig and the sliding base.

4. The apparatus for drop testing as claimed in claim 1, wherein the jig has an adjusting rod and an elastic element, the elastic element providing elastic strength for the holding frame to move towards the first predetermined position, and the adjusting rod limiting movement of the holding frame towards the first predetermined position.

5. The apparatus for drop testing as claimed in claim 4, wherein both sides of the holding frame are connected to a sliding element, and both sides of the jig respectively have a vertical sliding rail for vertical movement of the sliding element.

6. The apparatus for drop testing as claimed in claim 1, wherein both sides of the holding frame are connected to a sliding element, and both sides of the jig respectively have a vertical sliding rail for vertical movement of the sliding element.

7. The apparatus for drop testing as claimed in claim 1, wherein the bottom of the support frame has a plurality of adjusting feet for adjusting a horizontal level of the horizontal sliding rail.

8. The apparatus for drop testing as claimed in claim 1, wherein the test object is a long strip-shaped memory module.

9. The apparatus for drop testing as claimed in claim 1, wherein the first datum plane and the second datum plane are perpendicular to each other.

10. The apparatus for drop testing as claimed in claim 1 further comprising a clamping base used for combining with the fixture.

11. The apparatus for drop testing as claimed in claim 1, wherein the fixture has an opposing L shape and provides a first clamping face and a second clamping face, a clamping clearance of the first clamping face being smaller than a clamping clearance of the second clamping face, and the first clamping face away from the first datum plane.

12. The apparatus for drop testing as claimed in claim 1, wherein a gap is formed between the first datum plane in the first predetermined position and the second datum plane in the second predetermined position.

13. The method as claimed in claim 12, wherein when lowering the holding frame and moving the jig horizontally, the test object is held still and has no contact with the holding frame and the jig.

14. A method of using the apparatus for drop testing claimed in claim 1 comprising:
    adjusting the holding frame and the jig such that the first datum plane is moved to the first predetermined position and the second datum plane is moved to the second predetermined position;
    placing a test object on the jig, a first surface of the test object touching the first datum plane, and a second surface of the test object touching the second datum plane;
    utilizing the fixture to fix the test object;
    lowering the holding frame such that the first datum plane is moved to the first pull-back position without touching the test object, the test object touching the second datum plane of the jig;
    moving the jig horizontally such that the second datum plane is moved to the second pull-back position without touching the test object; and
    releasing the test object.

* * * * *